US00PP12294P2

(12) United States Plant Patent
Holland

(10) Patent No.: US PP12,294 P2
(45) Date of Patent: Dec. 18, 2001

(54) LILAC PLANT NAMED 'BAILBELLE'

(75) Inventor: Neal S. Holland, Harwood, ND (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 09/456,394

(22) Filed: Dec. 8, 1999

(51) Int. Cl.[7] ..... A01H 5/00
(52) U.S. Cl. ..... Plt./248
(58) Field of Search ..... Plt./248

*Primary Examiner*—Bruce R. Campell
*Assistant Examiner*—June Hwu

(74) *Attorney, Agent, or Firm*—Burns, Doane, Swecker & Mathis, L.L.P.

(57) ABSTRACT

A new and distinct highly ornamental variety of *Syringa meyeri*×*Syringa microphylla* is provided. A Lilac plant having a neat and compact growth habit is described. Highly attractive trusses of wine-colored buds are formed which open during late spring to display pink blossoms having a spicy fragrance. Good winter hardiness is made possible and the plant has been relatively free of insect and disease problems during observations to date. The plant is particularly well-suited for growing as an ornamental specimen or as a mass planting in the landscape.

3 Drawing Sheets

SUMMARY OF THE INVENTION

The new Lilac plant of the present invention was created at Harwood, N. Dak., by the cross of *Syringa meyeri* 'Palibin' (non-patented in the United States) and *Syringa microphylla* 'Superba' (non-patented in the United States). The parentage can be summarized as follows:

'Palibin'×'Superba'

Seed from the cross was collected during 1976, was planted, and the resulting plants were observed. A single plant of new cultivar was selected during 1985 in view of its distinctive ornamental characteristics. This plant initially was designated 'No. 85-1'.

It was found that the cultivar of *Syringa meyeri*×*Syringa microphylla* exhibits the following combination of characteristics:

(a) Exhibits a compact growth habit,
(b) Forms attractive trusses of wine-colored buds that mature during late spring into pick blossoms having a spicy fragrance,
(c) Exhibits good winter hardiness, and
(d) Is well-suited for growing as a distinctive ornamental shrub in the landscape.

The new cultivar of the present invention provides a highly distinctive blossom coloration to the landscape that is displayed in late spring after many other shrubs have finished flowering. It can be grown to advantage as a specimen shrub or as a part of a mass planting. The superior hardiness of the *Syringa meyeri* 'Palibin' parent which generally is lacking in the *Syringa microphylla* 'Superba' parent is well imparted to the new cultivar of the present invention.

The new cultivar of the present invention was asexually propagated by the use of rooted cuttings at St. Paul, Minn., during 1992, and the progeny were field planted during 1993. The distinctive characteristics of the new cultivar have been found to be stable and to be capable of transmission from one generation to another following such asexual propagation.

The new cultivar of the present invention has been named 'Bailbelle'. It is a member of the FAIRYTALE™ Series of Lilac plants, and is being marketed under the TINKERBELLE trademark.

BRIEF DESCRIPTION OF THE PHOTOGRAPHS

The accompanying photographs show, as true as reasonably possible to make the same in color illustrations of this character typical plants of the new cultivar. The plants were propagated by use of rooted cuttings and were photographed when approximately three years of age while growing in the field at St. Paul, Minn.

Figure 1:
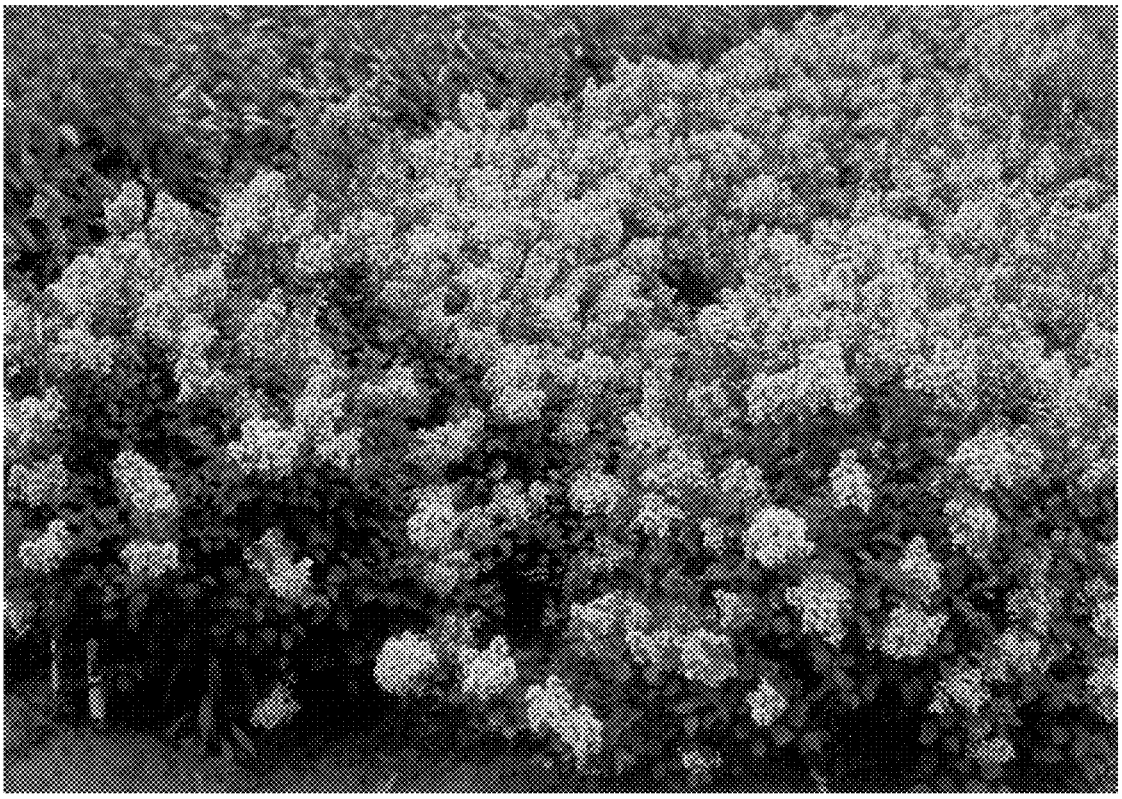

FIG. 1—shows blossoming plants wherein the neat and compact growth habit of the new cultivar is exhibited.

Figure 2:
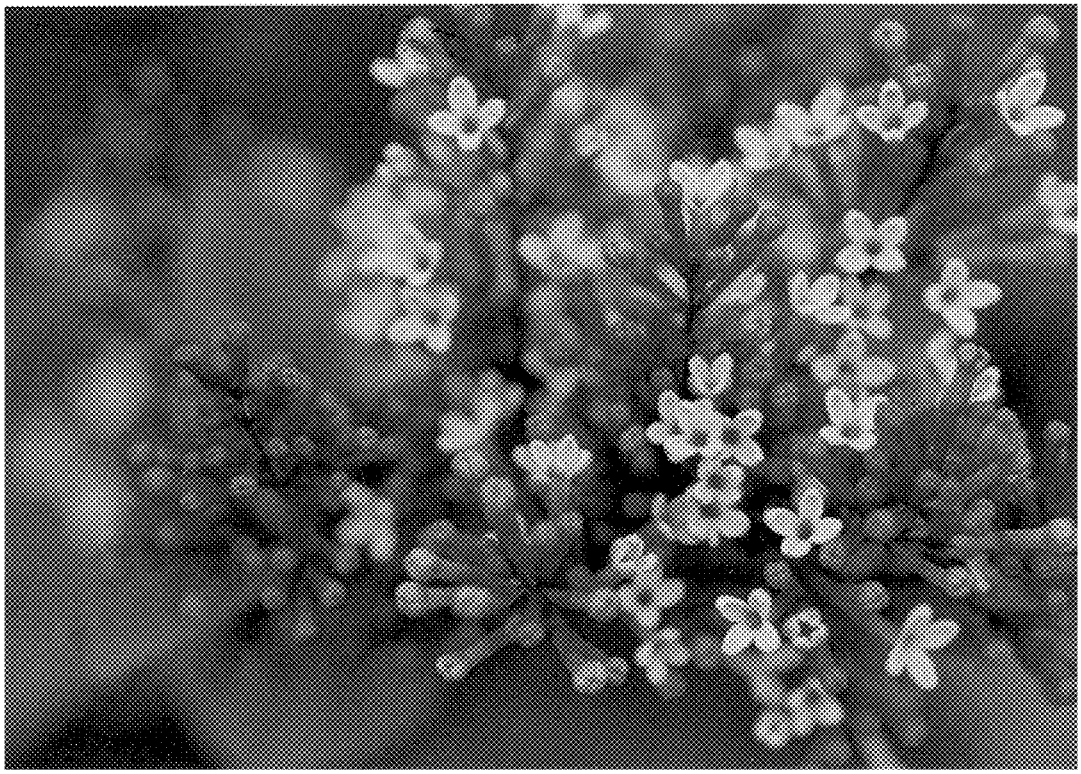

FIG. 2—shows a close up view of a truss of the wine-red buds with some lighter pink open blossoms during mid- to late-spring.

Figure 3:
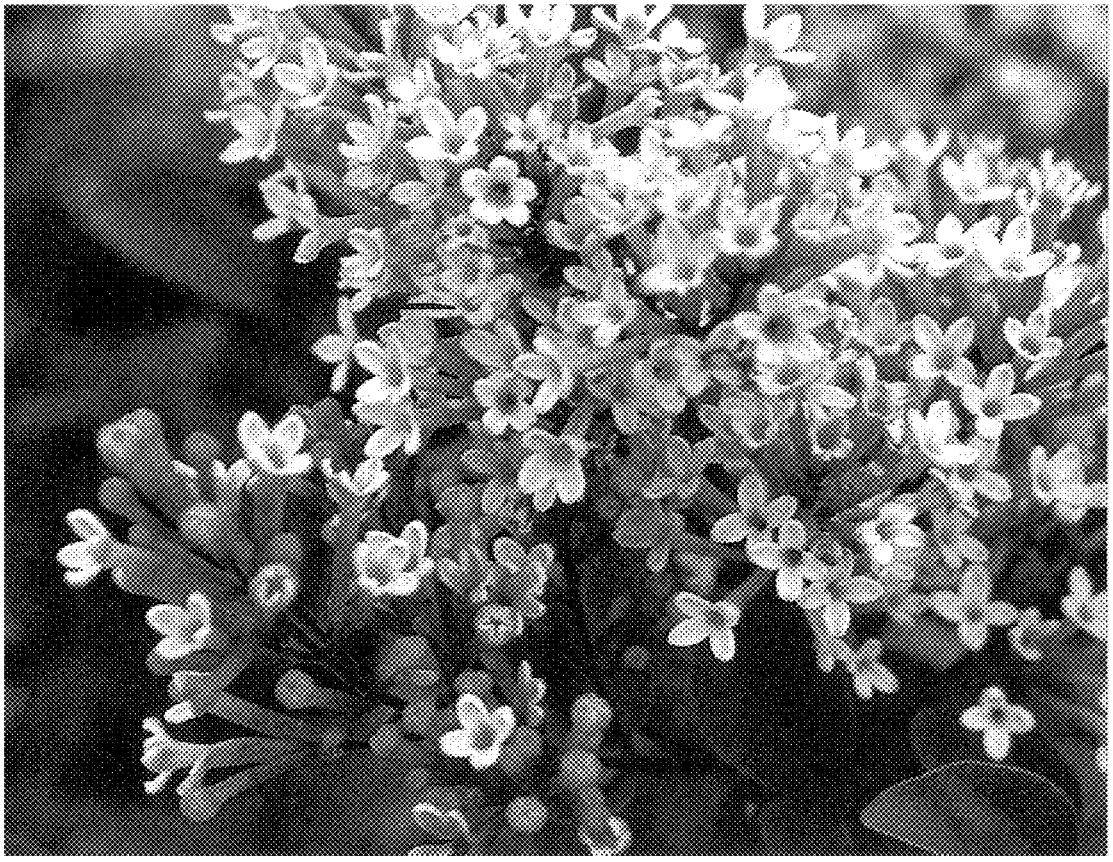

FIG. 3—shows a close up view of a truss of largely open pink blossoms with some foliage during late-spring. The wine red coloration of the new buds depicted in FIG. 3 is believed to be more accurate than the coloration of the corresponding buds shown in FIG. 2.

DETAILED DESCRIPTION

The chart used in the identification of colors in The R.H.S. Colour Chart of The Royal Horticultural Society, London. Common terms are to be accorded their ordinary dictionary significance. The description is based upon the observation of plants propagated by the use of rooted cuttings and growing in the field at St. Paul, Minn.

Botanical classification: *Syringa meyeri*×*Syringa microphylla*, 'Bailbelle'.

Plant:

*Growth habit*.—Compact shrub, and more upright than the *Syringa meyeri*, 'Palibin' parent.

*Size*.—Forms a shrub of approximately 5 to 6 feet in height and width.

Bark:

*Texture*.—Glabrous.

*Color*.—Greyed-Green Group 197A.

Foliage:

*Leaf shape*.—Elliptic/ovate.

*Leaf apex*.—Acute to obtuse.

*Leaf base*.—Rounded.

*Leaf margins*.—Entire.

*Color*.—Deep green, Green Group 137A (upper surface) and Green Group 137D (under surface). This can be compared to Green Group 139A (upper surface) for the *Syringa meyeri* 'Palibin' parent.

*Size*.—The leaves are approximately 1½ to 2½ inches in length and approximately 1¼ to 2 inches in width. This compares to a generally lesser length of approximately ¾ to 1¾ inches and a generally lesser width of approximately ¾ to 1⅜ inches for the 'Palibin' parent.

*Petioles*.—Commonly display a rugose surface texture, lengths of approximately 0.5 to 0.75 cm, and a coloration of Green Group 138B on the upper surface and Green Group 138C on the under surface.

*Stems*.—Rugose and appear more silvery than 'Palibin'. By comparison 'Palibin' exhibits tomentose stems. The coloration is Green Group 138B on the upper surface and Greyed-Green Group 197B on the under surface.

*Lenticels*.—Commonly are present on stems and measure approximately 0.1 to 0.3 cm, and are Grey-Brown Group 199D in coloration.

*Leaf midribs*.—Tomentose on the underside as is the midrib of 'Palibin'.

*Leaf venation*.—Pinnate with two or three pairs from the midrib to the margin.

*Leaf surface*.—Slightly duller on the upper surface than the glossy leaves of 'Palibin'. The under surface is glabrous while 'Palibin' displays some hairs on the lower surface.

Inflorescence:

*Arrangement*.—In panicles.

*Buds*.—In trusses, deep wine red, Red-Purple Group 71B when first appear and fade with lightening coloration.

*Flower configuration*.—Tubular with four petal lobes at the end (as illustrated).

*Flower size*.—Florets are approximately 1.0 to 1.5 cm in length and 0.2 to 0.6 cm in diameter at widest point. Panicles commonly measure approximately 3 to 5 inches.

*Flower color*.—With maturity fades from the deep wine red (Red-Purple Group 71B) of the buds to light red including Red-Purple Group 73C to lighter pink (near Red-Purple Group 69D) approaching white (near White-Group 155A) except for the center (as illustrated). The petal lobes tend to fade faster than the corolla tube.

*Stamens*.—Two.

*Filaments*.—Approximately 0.6 to 0.7 cm in length and Red-Purple Group 65D in coloration.

*Anthers*.—Red-Purple Group 64A in coloration.

*Pistil*.—Approximately 0.3 cm in length.

*Style*.—Red-Purple Group 62D in coloration.

*Stigma*.—Yellow-Green Group 150D in the absence of pollen and Yellow-Green Group 154D with pollen.

*Calyx*.—Cup-shaped with an entire lobe, rugose, approximately 0.2 cm in size, initially Green Group 138B in coloration and changing with maturity to Red-Purple Group 58A with highlights of Red-Purple Group 59D.

*Fragrance*.—Spicy.

*Flowering time*.—Mid- to late-spring.

Hardiness: Can be grown in U.S.D.A. Hardiness Zone Nos. 3 to 7. Possesses the superior hardiness of its *Syringa meyeri* parent and withstands the winter damage experienced by its *Syringa microphylla* parent which commonly is not reliably hardy in many areas. It has survived winters well during 1976 to 1993 at Harwood, N. Dak. which is on the border between U.S.D.A. Zone Nos. 3B and 4A. It also has wintered well when tested at St. Paul, Minn., and at Portage La Prairie, Manitoba, Canada. The later is in U.S.D.A. Zone No. 3B. In contrast the *Syringa microphylla* parent is considered to be hardy in U.S.D.A. Zone No. 5, and cannot winter successfully in the St. Paul, Minn., area over an extended period of time.

Culture: Similar to the Dwarf Korean Lilac. Prefers well-drained soil and a sunny growing location. Generally does not well tolerate poorly drained growing conditions.

Disease/pest resistance: Has proven to be relatively free of disease and insect problems during observations to date.

Landscape usage: Provides a hardy highly ornamental shrub having a distinctive blossom coloration and fragrance that can be grown as a specimen plant or in a mass planting.

I claim:

1. A new and distinct *Syringa meyeri*×*Syringa microphylla* plant having the following combination of characteristics:

(a) Exhibits a compact growth habit, (b) Forms attractive trusses of wine-colored buds that mature during late spring into pink blossoms having a spicy fragrance, (c) Exhibits good winter hardiness, and (d) Is well-suited for growing as a distinctive ornamental shrub in the landscape;

substantially as illustrated and described.

* * * * *